United States Patent [19]

Conrad

[11] 4,375,432
[45] Mar. 1, 1983

[54] METHOD OF PREPARING VINCRISTINE

[75] Inventor: Robert A. Conrad, Indianapolis, Ind.

[73] Assignee: Eli Lilly and Company, Indianapolis, Ind.

[21] Appl. No.: 321,662

[22] Filed: Nov. 16, 1981

Related U.S. Application Data

[63] Continuation-in-part of Ser. No. 262,836, May 12, 1981, abandoned, which is a continuation-in-part of Ser. No. 136,617, Apr. 2, 1980, abandoned.

[51] Int. Cl.$^3$ ............................................. C07D 519/04
[52] U.S. Cl. .................................................. 260/244.4
[58] Field of Search ..................................... 260/244.4

[56] References Cited

U.S. PATENT DOCUMENTS

| | | | |
|---|---|---|---|
| 3,354,163 | 11/1967 | Gorman | 260/244.4 |
| 3,899,493 | 8/1975 | Jovanovics et al. | 260/244.4 |
| 4,110,330 | 8/1978 | Barnett et al. | 260/244.4 |
| 4,195,022 | 3/1980 | Thompson | 260/244.4 |
| 4,298,525 | 11/1981 | Jovanovics et al. | 260/244.4 |
| 4,310,528 | 1/1982 | Jovanovics et al. | 424/262 |

OTHER PUBLICATIONS

Kutney, et al., Heterocycles, vol. 9, No. 2, pp. 201–206 (1978).

Primary Examiner—Donald G. Daus
Assistant Examiner—Diana G. Rivers
Attorney, Agent, or Firm—James L. Rowe; Arthur R. Whale

[57] ABSTRACT

VLB, 4'-deoxyleurosidine, leurosine and related 1-methyl vinca dimers are oxidized to vincristine-type compounds in tetrahydrofuran solution employing an aqueous chromate-sulfuric acid solution.

13 Claims, No Drawings

METHOD OF PREPARING VINCRISTINE

CROSS-REFERENCE

This application is a continuation-in-part of my copending application Ser. No. 262,836 filed May 12, 1981, now abandoned, which was a continuation-in-part of my then copending application Ser. No. 136,617 filed Apr. 2, 1980, now abandoned.

BACKGROUND OF THE INVENTION

The alkaloids obtainable from Vinca rosea represent one of the most productive sources of drugs which adversely affect the growth of experimental malignancies in mammals. Initially, only some of the alkaloids obtainable from the leaves of the plant by extraction and chromatography were found to be active as oncolytic agents. These active anti-neoplastic vinca alkaloids obtained directly from the plant have all turned out to be dimeric indole-dihydroindole alkaloids representable by the formula:

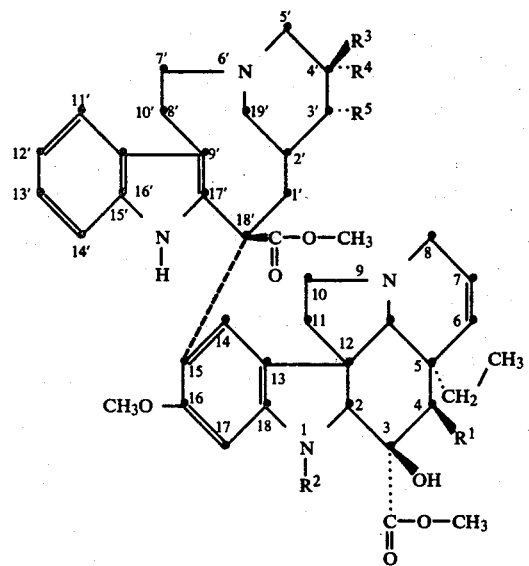

I

In the above formula, where $R^1$ is acetoxy, $R^2$ is methyl, $R^3$ is hydroxyl, $R^4$ is ethyl and $R^5$ is H, VLB (vincaleucoblastine, vinblastine) is represented; where $R^1$ is acetoxy, $R^2$ is formyl, $R^3$ is hydroxyl, $R^4$ is ethyl and $R^5$ is H, vincristine (VCR, leurocristine) is represented; where $R^1$ is acetoxy, $R^5$ is methyl, $R^3$ is ethyl, $R^4$ is hydroxyl, and $R^5$ is H, leurosidine (vinrosidine) is represented; where $R^1$ is acetoxy, $R^2$ is methyl, $R^3$ is ethyl, and $R^4$ and $R^5$ are H, 4'-deoxyleurosidine (deoxy VLB"B") is represented; where $R^1$ is acetoxy, $R^2$ is methyl, $R^4$ is ethyl and $R^3$ and $R^5$ are H, 4'-deoxy VLB (deoxy VLB"A") is represented; where $R^1$ is acetoxy, $R^2$ is methyl or formyl, $R^3$ is ethyl and $R^4$ and $R^5$ taken together with a bridging oxygen form an α-epoxide ring, leurosine (vinleurosine), and formylleurosine (leuroformine), respectively, are represented. Literature references to the above alkaloids are as follows: leurosine (U.S. Pat. No. 3,370,057), VLB (U.S. Pat. No. 3,097,137), formylleurosine (leuroformine) (U.S. Pat. No. 4,189,432); leurosidine and leurocristine (both in U.S. Pat. No. 3,205,220), and deoxy VLB"A" and "B", Tetrahedron Letters, 783 (1968).

Two of the above alkaloids, VLB and vincristine, are now marketed for the treatment of malignancies, particularly the leukemias and related diseases in humans. The two marketed alkaloids are customarily administered by the i.v. route. Two others, leurosidine and formylleurosine, have been on clinical trial, either in the U.S. or in Europe.

VLB is more abundant than vincristine, being isolatable in usually eight to ten-fold greater quantities. Methods of converting VLB to vincristine are therefore highly desirable, and much research time and considerable resources have been expended looking for such procedures.

As is the case with the pair VLB-vincristine, the pair leurosine-formylleurosine is characterized by the greater abundance of the N-methyl derivative—leurosine—in the crude alkaloid mixture obtained from Vinca rosea leaves. Use of formylleurosine in treating lymphoid leukemia, lymphoma, Hodgkin's disease and multiple myeloma are claimed in U.S. Pat. Nos. 4,279,916, 4,279,915 and 4,279,816.

To date, only three methods of converting VLB to vincristine have appeared in the literature. These are: enzymatic oxidation with a peroxidase and $H_2O_2$, (Gorman-U.S. Pat. No. 3,354,163); catalytic oxidation with molecular oxygen at ambient temperature in formic acid (Derwent Abstract No. 33812Y/19 based on Soviet Union Pat. No. 521,845); and oxidation of VLB sulfate with chromic oxide in glacial acetic acid and acetone at −60° C. (U.S. Pat. No. 3,899,943). Vincristine yields of 50% based on recovered VLB are reported by the latter procedure.

The published procedures for producing formylleurosine by oxidation of leurosine or for producing 4'-deoxy-1-desmethyl-1-formylleurosidine by oxidation of 4'-deoxyleurosidine both involve a low temperature (−60° C.) process utilizing the $CrO_3$, acetone and acetic acid oxidation mixture first found useful for producing vincristine from VLB.

This chromic acid—acetone—acetic acid oxidation process at −60° C. is not without drawbacks, however. The maintenance of low reaction temperatures is difficult in a manufacturing plant, but higher temperatures produce increasing quantities of undesirable by-products. In addition, Barnett et al., U.S. Pat. No. 4,110,330, have found that, in the VLB-vincristine conversion, VLB reacts with acetone at C-5' under oxidizing conditions, even at −60° C., to yield 5'-acetonylvincristine and related products. Similar 5'-substitution products are produced in oxidizing leurosine or 4'-deoxyleurosidine with this oxidizing system.

These undesirable 5'-VCR derivatives encountered as by-products in the chromic acid oxidation of VLB sulfate in acetone are definite detriments to the use of that process in manufacturing vincristine from VLB. The 5'-acetonyl compounds are, of course, separable from vincristine by chromatography, but there is a consequent loss of the desired product, vincristine. Furthermore, during this oxidation, there are produced substantial quantities of N-desformyl vincristine which must be reformylated in order to maximize vincristine yields. Reformylation is an added, expensive procedure when oxidation results in deformylation as well as oxidation.

It is an object of this invention to provide a procedure for converting VLB, leurosine, 4'-deoxyleurosidine, 4-desacetyl VLB and related N-methyl vinca dimers to their respective vincristine-type compounds, which procedure avoids the drawbacks of the prior art procedures.

DESCRIPTION OF THE INVENTION

In fulfillment of the above and other objects, this invention provides a method of preparing a compound of the formula

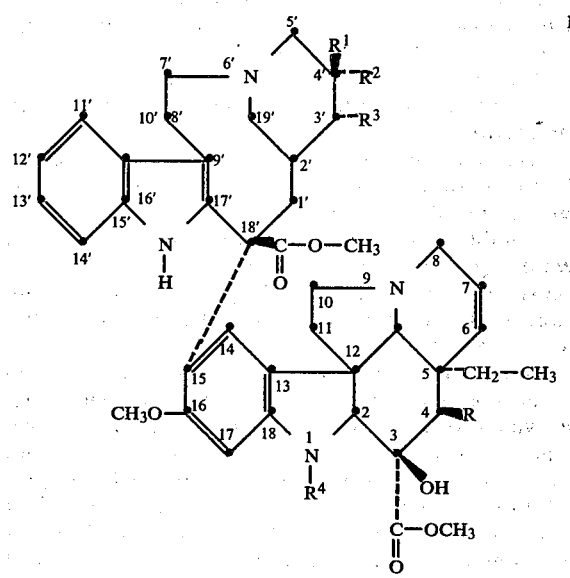

wherein, R is OH or acetoxy, $R^4$ is CHO, and when taken singly, one of $R^1$ and $R^2$ is H or OH and the other is $C_2H_5$ and $R^3$ is H and, when taken together, $R^2$ and $R^3$ with a bridging oxygen atom represent an α-epoxide and $R^1$ is $C_2H_5$; which comprises dissolving a compound according to Formula II, in which $R^4$ is $CH_3$ and R, $R^1$, $R^2$ and $R^3$ have their previously assigned significance, in tetrahydrofuran and contacting said solution with an aqueous chromate-sulfuric acid solution at a reaction temperature below about −50° C.

The preferred process for preparing an N-formyl vinca dimer (II when $R^4$ is CHO) comprises dissolving the starting material free base (II in which $R^4$ is $CH_3$) in tetrahydrofuran (THF), lowering the solution temperature to a temperature in the range −60° to −77° C., adding an aqueous dichromate-sulfuric acid mixture thereto while maintaining the temperature below about −50° C., stirring the reaction mixture below about −60° C. until substantially all the starting material initially present is converted to the N-formyl vinca dimer, (II wherein $R^4$ is CHO) and then recovering the N-formyl vinca dimer therefrom.

A preferred embodiment of my novel process involves the conversion of VLB to vincristine under the above reaction conditions. Vincristine obtained by this procedure can be readily purified to drug quality by using high pressure liquid chromatography over silica or alumina or a combination of these and/or by crystallization. Purified vincristine is customarily converted to the sulfate salt after chromatography and/or crystallization.

A second preferred embodiment of my novel process comprises the oxidation of leurosine to formylleurosine with the aqueous dichromate-sulfuric acid reagent in THF. High yields and fewer undesirable by-products are a feature of this embodiment of my novel process.

A third preferred embodiment of my novel process is the oxidation of 4′-deoxyleurosidine to 4′-deoxy-1-desmethyl-1-formylleurosidine. By-product formation with the low temperature $CrO_3$-acetone process is similar in nature and quantity to that encountered in the VLB-vincristine oxidation with $CrO_3$-acetone and, consequently, my novel process is equally desirable in the avoidance of these by-products when 4′-deoxyleurosidine is to be transformed to 4′-deoxy-1-desmethyl-1-formylleurosidine.

Alternatively, I have found that a crude vinca dimer alkaloid mixture (VRA), such as that obtained from Vinca rosea leaves by the process of paragraph 1 of Example 1 of U.S. Pat. No. 3,932,417, can be oxidized as such (without further alkaloid separation steps) with the aqueous chromate-sulfuric acid-THF oxidation system of this invention. The resulting 1-formyl derivatives can be separated from the crude reaction mixture and purified by chromatography, particularly high-pressure liquid chromatography. The VRA alkaloid mixture contains major amounts of two N-methyl vinca dimers—VLB and leurosine—with much smaller quantities of 4′-deoxy VLB, leurosidine, 4′-deoxyleurosidine, leurocolumbine, etc. Vincristine, an N-formyl vinca dimer, is present in 1/10 to 1/8 the quantity of VLB. Formylleurosine has also been isolated from VRA or a VRA-like fraction in small amounts.

Particularly with regard to vincristine, this alternate process requires only one alkaloid separation step, that carried out after the oxidation procedure whereas, with the standard procedure, vincristine and VLB would both be isolated from VRA, VLB would then be oxidized to vincristine and the vincristine again isolated from that reaction. The usual reformylation step would also be desirable to convert any desformyl congeners originally in the VRA and/or formed in the oxidation process to the corresponding N-formyl derivatives. It is apparent that my alternate oxidation procedure, utilizing a crude alkaloid mixture as substrate, is advantageous in that there is less handling required, a shorter time from leaf to product is attainable, etc. compared to the standard oxidation procedure. My novel oxidation process utilizing a chromate-sulfuric acid oxidizing mixture in THF at about −60° C. is particularly useful in oxidizing the crude dimeric alkaloid mixture (VRA) to obtain substantial quantities of vincristine and formylleurosine in that there is less handling, sampling and recycling plus fewer operations and a shorter time period compared to the prior art procedures. These advantages have been encountered in trial runs in comparison with the $CrO_3$-acetone-acetic acid process for converting VLB to vincristine.

In Formula II above VLB is represented when R is acetoxy, $R^1$ is OH, $R^2$ is $C_2H_5$, $R^3$ is H and $R^4$ is $CH_3$ and it is oxidized to vincristine (R is acetoxy, $R^1$ is OH, $R^2$ is $C_2H_5$, $R^3$ is H and $R^4$ is CHO). My novel procedure also includes the oxidation of leurosidine (R is acetoxy, $R^1$ is $C_2H_5$, $R^2$ is OH, $R^3$ is H and $R^4$ is $CH_3$) to 1-formyl-1-desmethylleurosidine (R, $R^1$, $R^2$ and $R^3$ are the same as before but $R^4$ is CHO), the oxidation of 4′-deoxy VLB ($R^1$ and $R^3$ are H, $R^2$ is $C_2H_5$, R is acetoxy and $R^4$ is $CH_3$) to 4′-deoxyvincristine ($R^1$ and $R^3$ are H, R is acetoxy, $R^2$ is $C_2H_5$ and $R^4$ is CHO), the oxidation of 4′-deoxyleurosidine ($R^2$ and $R^3$ are H, $R^1$ is $C_2H_5$, R is acetoxy and $R^4$ is $CH_3$ to 1-formyl-4′-deoxy-1-desmethylleurosidine ($R^2$ and $R^3$ are H, $R^1$ is $C_2H_5$, R is acetoxy and $R^4$ is CHO), the oxidation of leurosine ($R^1$ is $C_2H_5$, R is acetoxy, $R^2$ and $R^3$ plus a bridging oxygen atom form an α-epoxide group and $R^4$ is $CH_3$) to formylleurosine and the oxidation of 4-desacetyl VLB (R and $R^1$ are OH, $R^2$ is $C_2H_5$, $R^3$ is H, and $R^4$ is methyl) to 4-desacetylvincristine. In naming those 1-formyl compounds hereinafter which have no other trivial name, the term "1-desmethyl" will be omitted as understood; i.e., if a formyl group is present at N-1, the methyl group must necessarily be absent.

Sodium dichromate dihydrate has been found to be the preferred chromate for use in the above process although other dichromates or chromates such as $K_2Cr_2O_7$, $K_2CrO_4$, $Na_2CrO_4$, $CrO_3$ and the like can be employed. The term "chromate" as used herein includes all such species. The ratio of sodium dichromate dihydrate to anhydrous alkaloid should be in the range 1.5–2.0 to 1 (w/w). The quantity of THF customarily employed is about 100 to 200 times the amount (v/w) of VLB or leurosine or other alkaloid or mixture of alkaloids employed on an anhydrous basis with a ratio of about 150 to 1 (v/w) being preferred. Reaction temperatures can vary from about −80° C. (dry ice/acetone) to about −50° C. Best results are obtained, however, by employing an acetone/dry ice bath (−77° C.) to maintain the temperature below about −70° C. Temperatures below about −50° C., while not optimal, are fully operative. As will be recognized by those skilled in the art, the lower temperature limit is one at which the reaction mixture begins to solidify, which temperature is about −80° C. depending on the solutes present in THF.

A reaction time of about 2 hours is optimal although reaction times varying from 1–3 hours are fully operative. A wash of the oxidation mixture after the reaction is substantially complete with a reducing agent such as ferrous sulfate or sodium metabisulfite is advisable in order to remove peroxides or residual oxidant. In the oxidizing reagent, sulfuric acid has been specified and is preferred, although certain other strong acids such as perchloric acid are operative.

It has been determined that, while THF is superior to acetone-acetic acid as a solvent in the −60° C. chromic acid oxidation of VLB to vincristine, the combination of THF and sodium dichromate-sulfuric acid is unexacetic acid was added and a positive $N_2$ blanket provided. The solution temperature was lowered to about −61° C. (chloroform-dry ice) and an aqueous solution of a chromate salt or chromic acid was added slowly with stirring while keeping the temperature below about −55° C. The mixture was stirred for about 3 hours at −61° C. after the addition had been completed. The reaction mixture was worked up as follows: the reaction mixture was added to 35 ml. of 14 N aqueous ammonium hydroxide in 200 ml. $H_2O$. The alkaline solution was extracted 3 times with 200 ml. portions of $CH_2Cl_2$. The extracts were combined, dried over anhydrous sodium sulfate, filtered and the solvents removed by evaporation. The residue was assayed for vincristine, desformylvincristine and VLB. The reaction conditions, which were varied, are given in Table 1 as well as alkaloid yields. In Table 1 column 1 gives the reaction symbol (A-D), column 2, the solvent, column 3, mls of glacial acetic acid added, column 4, the oxidizing mixture used, and columns 5–7, percent yields of vincristine, desformylvincristine and VLB. Percent yields calculated were based on assayed material, molecular weight change and purity of starting material.

Reformylation using an acetic anhydride-formic acid mixture for 1 hour at ambient temperature gave the following total vincristine yields for runs having appreciable desformyl vincristine by-product.

B: 53.3%
C: 79.8%
D: 64.8%

According to the data presented in the Table, although THF has advantages over glacial acetic acid-acetone as a solvent—at the minimum, a lack of 5′-acetonyl formation—the combination of THF and a chromate salt, preferably sodium dichromate, is unexpectedly superior to a combination of THF and chromic oxide in the oxidation of VLB in that the yields of vincristine are higher, and neither desformyl vincristine nor VLB are present in detectable quantities. The absence of N-desformyl vincristine removes the necessity for a separate reformylation step, as has been set forth above.

TABLE 1

| Reaction Symbol | Solvent | Glacial acetic acid mls | Oxidizing Mixture | Percent yield | | |
|---|---|---|---|---|---|---|
| | | | | vincristine | desformyl vincristine | VLB |
| A[4]** | 240 ml. THF | 7.5* | 3.0 g. $Na_2Cr_2O_7$ 15 ml. $H_2O$ 2 ml. 18M $H_2SO_4$ | 91.2 | 0 | 0 |
| B[1] | 20 ml. $CH_2Cl_2$ 220 ml. acetone | 7.5* | 3.0 g. $Na_2Cr_2O_7$ 15 ml. $H_2O$ 2 ml. 18M $H_2SO_4$ | 30.9 | 11.9 | 19.1 |
| C[2] | 240 ml. THF | 7.5 | 2.0 g. $CrO_3$ 4.0 ml. $H_2O$ 20.0 ml. HOAc | 62.3 | 17.7 | 0 |
| D[1] | 20 ml. $CH_2Cl_2$ 220 ml. acetone | 7.5 | 2.0 g. $CrO_3$ 4.0 ml. $H_2O$ 20.0 ml. HOAc | 52.5 | 12.0 | 0 |

*Acetic acid can be omitted from $Cr_2O_7^{-2}$ oxidations - see Table 3.
**1st column super scripts = no. of runs.

pectedly superior to the use of either THF with chromic acid or acetone with dichromate, as the experimental results demonstrate. The following oxidation protocol was used in demonstrating the superiority of my novel process as applied to VLB over the prior art processes:

A two gram sample of VLB base (assayed for VLB content) prepared from VLB sulfate was dissolved in a given quantity of solvent as indicated in Table 1. Glacial A similar improvement in yield has also been obtained using the sodium dichromate/tetrahydrofuran (THF) process in transforming leurosine (vinleurosine, VLR) into formylleurosine (leuroformine, FVLR) as compared with a modified Richter chromium trioxide-/acetone low temperature process.

The modified Richter process utilized for comparative purposes (Table 2-F) follows: Leurosine base, 5.0 g., was dissolved in 50 ml. methylene chloride after which 550 ml. acetone was added. A nitrogen purge and blanket were applied and the temperature of the solution was lowered to a temperature in the range −60° to −70° C. using a dry ice-chloroform bath. A solution of 5 g. chromium trioxide in 10 ml. water and 50 ml. glacial acetic acid was added over a period of 10 minutes. The reaction was stirred for 120 minutes with the temperature ranging from −59° to −68° C. The reaction mixture was added to a solution of 100 ml. 28% ammonium hydroxide in 500 ml. water. The solution was extracted three times each with 300 ml. methylene chloride. The organic extracts were combined and evaporated in vacuo yielding 4.55 g. crude formylleurosine which was assayed for product content.

TABLE 2

| Reaction Symbol | Solvent | Oxidizing Mixture | Percent yield* Formyl-leurosine | Major Impurities |
|---|---|---|---|---|
| E | 600 ml. THF | 6.25 g. $Na_2Cr_2O_7$ 37.5 ml. $H_2O$ 4.5 ml. 18M $H_2SO_4$ | 90 | Not Detected |
| F | 50 ml. $CH_2Cl_2$ 550 ml. acetone | 5 g. $CrO_3$ 10 ml. $H_2O$ 50 ml. HOAc | 43 | 50–55** |

*The crude product and the reaction residues were assayed by analytical HPLC. In a like manner, the starting material, and a reference sample of formylleurosine were also analyzed. The yields reported below are therefore based both on weight yields and purities of the products, starting material, and reference; no molecular weight considerations have been made.
**Probably the 5'-acetonyl-type product seen in the Richter oxidation but possibly N—desmethyl leurosine.

It is noted that the yield comparison in Table 2 gives numbers very similar to those seen in the respective VLB/VCR conversions in Table 1.

From both the HPLC and TLC profiles, it is quite obvious that under the reaction conditions previously mentioned, the sodium dichromate/THF reaction is far superior in all aspects to the modified Richter process. The Richter conditions used in this experiment were modified as they were in the VLB experiments due to the difference in starting material (i.e., free base instead of sulfate salt) and general improvements (reduced volumes, improved workup, etc.). Yields of VCR or of leurosine are better with this modified Richter process than those set forth in the Richter U.S. Pat. Nos. 3,899,943 and 4,189,432.

There would seem to be little doubt, however, that, just as with the oxidation of VLB, the dichromate/THF conditions applied to the oxidation of leurosine give better yields, less over— and under—reaction, and fewer by-products (especially 5'-acetonyl derivatives) than the Richter process.

The following further examples illustrate the above process.

EXAMPLE 1

2 g. of VLB free base prepared from the sulfate salt were dissolved in 240 ml. of THF. 7.5 ml. of glacial acetic acid were added and the mixture cooled to about −65° C. by means of a chloroform/dry ice bath under a positive nitrogen blanket. Next, over a 1-2 minute period, a solution (prepared by dissolving 3 g. of sodium dichromate dihydrate in 15 ml. of water and then adding 2 ml. of 18 M sulfuric acid) was added slowly with stirring to the VLB free base solution while maintaining the reaction temperature below about −50° C. The reaction mixture was stirred for an additional 3 hours while maintaining the temperature at about −65° C. and was then poured into a solution containing 35 ml. of 14 M aqueous ammonium hydroxide in 200 ml. of water. The solution was extracted 3 times with 200 ml. portions of methylene chloride. The organic extracts were combined and dried. Evaporation of the solvent gave as a residue 2.05 g. of crude vincristine containing no detectable VLB or N-desformyl vincristine. Yield of vincristine was 91.2% (average of Runs 1-4 Table 3) corrected for purity of starting material and assay of final product for vincristine.

The following table, Table 3, gives the results of a series of runs carried out more or less as set forth above. In the table, column 1 gives the number of the run, column 2 the assayed weight of VLB in grams, column 3 the crude weight of vincristine in grams, column 4 percentage of vincristine by assay, column 5 theoretical grams of vincristine which would be produced from the crude vincristine, and column 6 percent yield of vincristine based on assayed VLB.

Runs 1-4 were carried out as in the above example. Runs 5 and 6 were the same as Runs 1-4 except that acetic acid was omitted. Runs 7-8 were the same as Runs 5-6 except that only 200 ml. of THF were used. Runs 9-12, were the same as Runs 7-8 except that there was an added step of washing the combined organic extracts with a ferrous sulfate solution (5 g./100 ml. of water) prior to work-up.

TABLE 3

| Run No. | Assayed weight of VLB in g. | Crude Weight vincristine in g. | Percent vincristine by Assay | Grams of vincristine | Percent yield of vincristine |
|---|---|---|---|---|---|
| 1 | 1.80 | 2.09 | 84.5 | 1.77 | 96.4 |
| 2 | 1.80 | 2.06 | 81.4 | 1.68 | 91.6 |
| 3 | 1.80 | 2.08 | 79.7 | 1.66 | 90.6 |
| 4 | 1.81 | 2.07 | 76.8 | 1.59 | 86.3 |
| 5 | " | 2.07 | 84.7 | 1.75 | 95.2 |
| 6 | " | 2.03 | 74.4 | 1.51 | 82.0 |
| 7 | " | 1.99 | 82.5 | 1.64 | 89.2 |
| 8 | " | 1.98 | 74.2 | 1.47 | 79.8 |
| 9 | " | 2.01 | 86.8 | 1.74 | 94.8 |
| 10 | " | 2.00 | 81.7 | 1.63 | 88.7 |
| 11 | " | 1.89 | 79.5 | 1.50 | 81.6 |
| 12 | " | 1.88 | 82.7 | 1.55 | 84.4 |

In all of the above experiments employing THF as a solvent, the quantity of N-desformyl vincristine present was less than 1 percent as was the amount of unreacted VLB starting material. Thus, the above yields are direct yields and are not based upon either recovered VLB starting material or upon vincristine prepared by an added step of formylating the reaction by-product, N-desformyl vincristine. In addition, of course, no 5'-acetonyl vincristine by-products were found since acetone was not used as a solvent.

The above shows that acetic acid is not only not required in the oxidation of an N-methyl in a vinca dimer, but also that yields are as good or better in its absence using THF as the sole solvent.

In each of the above runs, VLB base was prepared from VLB sulfate. The VLB free base samples, isolated from VLB sulfate, were assayed for VLB free base content. The theoretical yield of vincristine was based upon the assayed quantity of VLB base present initially. Thus, for each run 2.00 g. of VLB base "as is" were used. Column 2 in Table 3 reports actual VLB base present in each 2.00 g. sample, typically about 90%. The difference between actual and assayed amount is primarily due to the presence of volatiles.

EXAMPLE 2

A similar oxidation to that of Example 1 was carried out employing a 2.00 g. batch of VLB base which assayed at 78.4 percent, giving an actual quantity of VLB present by assay of 1.57 g. The VLB was dissolved in 240 ml. of THF as before and no acetic acid was used. The reaction mixture was cooled with a chloroform/dry ice bath (−65° C.). The oxidizing solution consisted of 2.5 g. of sodium dichromate dihydrate and 15 ml. of water plus 1.7 ml. of 18 M sulfuric acid. The vincristine was isolated as in Example 1 except that the combined organic extracts were washed with 5% aqueous sodium metabisulfite at the rate of 2.5 g./50 ml. (substituted for the ferrous sulfate wash of runs 9-12 in Table 3) prior to work-up.

Yields of upwards of 98 percent vincristine by assay have been routinely obtained by following the above procedure. In one large scale run using 20 g. of 78.9% pure VLB base, an assay yield of 93.4% of vincristine was obtained.

EXAMPLE 3

Leurosine base, 5.0 g., was dissolved in 600 ml. tetrahydrofuran (THF). A nitrogen purge and blanket were applied and the temperature of the solution was lowered to a temperature in the range −70° to −77° C. using a dry ice-acetone bath. A solution of 6.25 g. sodium dichromate in 37.5 ml. water and 4.5 ml. concentrated sulfuric acid was added over a period of 10 minutes. The reaction was stirred for 120 minutes with the temperature ranging from −70° to −77° C. The reaction was removed from the bath and a solution of 37.5 ml. 28% ammonium hydroxide in 500 ml. water was added. The solution was extracted three times each with 300 ml. methylene chloride. The pooled organic extracts were washed with a solution of 6.25 gm. sodium metabisulfite in 125 ml. water and then evaporated in vacuo to yield 5.24 g. crude formylleurosine. The crude product was assayed along with the starting material and a reference sample by HPLC. The yield of 89.9% was determined based on weight yields, and purities of the products and starting materials without taking molecular weights into consideration.

EXAMPLE 4

Following the procedure of the above Example, 6.3 g. of 4-desacetyl VLB was oxidized in THF solution with sodium dichromate-sulfuric acid to yield 3.6 g. of purified 4-desacetyl vincristine.

EXAMPLE 5

Four 10 g. samples of VRA (a crude alkaloid mixture produced by extraction from *Vinca rosea* leaves using the procedure of U.S. Pat. No. 3,932,417) were treated as follows:

A. HPLC over alumina to produce VLB fraction; HPLC over silica to produce purified (98+%) VLB; conversion to VLB sulfate.

B. Same as A but preceded by reformylation step.

C. Oxidation by procedure of Example 2 (approximately 5× the quantity of oxidation mixture); HPLC over alumina to produce vincristine fraction; HPLC over silica to produce purified vincristine; conversion to vincristine sulfate.

D. Same as C but formylation step between oxidation and HPLC over alumina.

Table 4 below summarizes these four runs. In the Table, column 1 gives the VLB sulfate yields, column 2 the yield of vincristine sulfate to be expected from the amount of 1-desformylvincristine (DFVCR) present and column 3, the vincristine (VCR) sulfate yields, all as a percent of VRA free base. For the alkaloids isolated but present in quantities too small for practical subsequent purification, the final yields were extrapolated based on prior runs using larger amounts of the same type of material.

TABLE 4

| Run | VLB.SO$_4$ | VCR.SO$_4$ from DFVCR | VCR.SO$_4$ |
|---|---|---|---|
| A | 34.6% | 1.7%* | 4.0%* |
| B | 31.0% | ND | 5.8%* |
| C | ND | 0.4%* | 33.1% |
| D | ND | ND | 29.4% |

ND = none detectable
*= extrapolated from an average of plant production and laboratory scale runs using larger quantities of VRA.

Final yields of purified alkaloid are necessarily lower because of handling losses, purification losses and amount not recoverably present in other fractions. Formylleurosine, produced by oxidation of leurosine present in VRA (25-40% compared to VLB 40-45% by analysis of crude mixture), is obtained from the HPLC column as a fraction ahead of vincristine. The formylleurosine fraction is then further purified by a second HPLC procedure.

The above figures would indicate that vincristine yields by my novel oxidation process are at least equal to those obtainable by standard procedures. For example, the yield of VCR expected from oxidation of VLB by my procedure would be about 27.7% in A (80% yield) plus desformylvincristine and vincristine=33.- 4%—the actual yield was 33.1%.

In order to study further the oxidation of a crude alkaloid mix, a fifth run (E) was carried out on a 4× scale (40 g of VRA) following the D protocol. The results of this run are given in Table 5, with column heading same as Table 4.

TABLE 5

| Run | VLB.SO$_4$ | VCR.SO$_4$ from DFVCR | VCR.SO$_4$ |
|---|---|---|---|
| E | ND | ND | 43.0% |
| VRA starting material* | 31% | 2.5% | 3.5% |

*= expected yields based on prior runs
ND = none detectable

Here, the total projected yield of VCR would be 80% conversion X 31% VLB=24.8%+2.5% DFVCR+3.5% VCR=30.8% total. Actual yield was 43.0%, far higher than the projected yield. Several possible explanations for this higher yield will spring to mind. First, oxidation of N-methyl vinca dimers to the corresponding N-formyl compounds simplifies the alkaloid mixture since the main components of the oxidation mixture are formylleurosine and vincristine whereas in VRA, these two desirable alkaloids (from the point of view of cancer chemotherapy) are grossly contaminated with VLB, leurosine and several minor N-methyl alkaloids. In other words, the HPLC purification mixture is much less complex than the VRA starting material. Secondly, when purifying VLB by chromatography, some VLB contaminates neighboring chromatographic fractions and is not available for oxidation when purified VLB is the substrate. However, much of the VLB thus lost can be recovered by pooling neighboring chromatographic fractions, VLB sulfate formation mother liquors, etc, and isolating the VLB therefrom. This VLB can in turn be oxidized to vincristine in 80% yield. Thus, the increase in vincristine yield is really an increase in mainstream yield and not necessarily in overall yield.

This increase in mainstream yield is particularly advantageous in that the cost of recovering VLB from mother liquors, adjacent chromatographic fractions, etc. and then converting the VLB to vincristine is far higher per gram of vincristine obtained than the cost per gram of mainstream material.

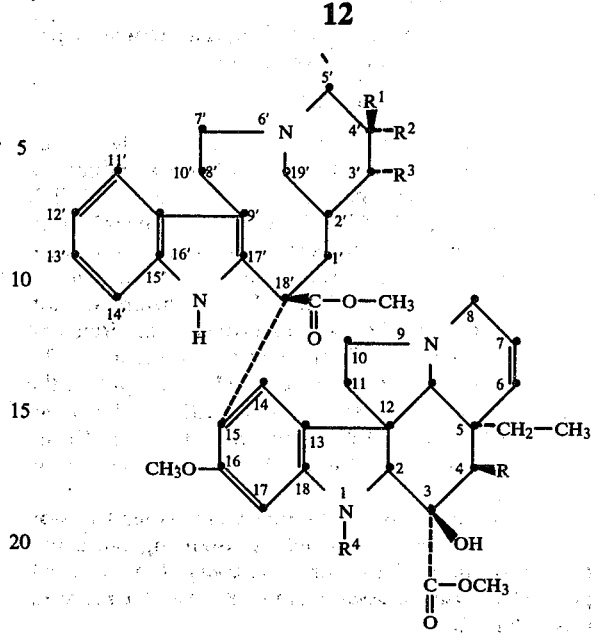

I claim:

1. The process of converting VLB to vincristine which comprises contacting a solution of VLB base in tetrahydrofuran (THF) with an aqueous chromate-sulfuric acid solution at a temperature in the range about $-80°$ C. to about $-50°$ C. until substantially all the VLB initially present is converted to vincristine and then isolating the vincristine therefrom.

2. A process according to claim 1 in which the ratio of THF to VLB base is in the range 100–200 to 1 (v/w).

3. A process according to claim 1 in which the ratio of THF to VLB base is about 150 to 1 (v/w).

4. A process according to claim 1 in which the source of chromate is sodium dichromate.

5. A process according to claim 4 in which the ratio of sodium dichromate to VLB base is about 1.5–2.0 to 1 on a weight basis.

6. A process according to claim 1 in which the reaction temperature is in the range $-80°$ C. to $-70°$ C.

7. A process according to claim 1 in which the ratio of 18 M sulfuric acid to VLB base is in the range 1.0–1.3 to 1.0 on a v/w basis.

8. In the chromic oxide-acetic acid oxidation of vinblastine to vincristine, the improvement which comprises employing tetrahydrofuran as the solvent for VLB base.

9. The method of preparing a compound of the formula wherein, R is OH or acetoxy, $R^4$ is CHO, and when taken singly, one of $R^1$ and $R^2$ is H or OH and the other is $C_2H_5$ and $R^3$ is H and, when taken together, $R^2$ and $R^3$ with a bridging oxygen atom represent an α-epoxide and $R^1$ is $C_2H_5$;
which comprises dissolving a compound according to Formula II, in which $R^4$ is $CH_3$ and R, $R^1$, $R^2$ and $R^3$ have the same significance as before, in tetrahydrofuran and contacting said solution with an aqueous chromate-sulfuric acid solution at a reaction temperature in the range from about $-80°$ C. to about $-50°$ C.

10. A process according to claim 9 by which leurosine is converted to formylleurosine.

11. A process according to claim 9 by which 4'-deoxyleurosidine is converted to 1-formyl-4'-deoxy-1-desmethylleurosidine.

12. A process according to claim 1 in which the VLB is present as part of a mixture which includes the unseparated dimeric indole-dihydroindole alkaloids obtained from Vinca rosea leaves by extraction.

13. A process for preparing VCR and formylleurosine which comprises oxidizing a tetrahydrofuran solution of the crude dimeric indole-dihydroindole alkaloids obtainable by extraction from the leaves of Vinca rosea in which VLB and leurosine are the predominant alkaloids with an aqueous chromate-sulfuric acid oxidizing solution at a temperature in the range about $-80°$ C. to about $-50°$ C. until substantially all the VLB and leurosine initially present are converted to vincristine and formylleurosine respectively, optionally reformylating any 1-desformyl congeners present, and then separating vincristine and formylleurosine therefrom by chromatography.

* * * * *